United States Patent [19]

Franz et al.

[11] 4,411,882

[45] Oct. 25, 1983

[54] GALENICAL COMPOSITIONS

[75] Inventors: Joachim Franz, Riehen, Switzerland; Ludwig Patt, Nuremberg, Fed. Rep. of Germany

[73] Assignee: Sandoz Ltd., Basel, Switzerland

[21] Appl. No.: 274,603

[22] Filed: Jun. 17, 1981

Related U.S. Application Data

[63] Continuation-in-part of Ser. No. 105,831, Dec. 20, 1979, abandoned.

[30] Foreign Application Priority Data

| Dec. 21, 1978 | [CH] | Switzerland | 13019/78 |
| Dec. 21, 1978 | [CH] | Switzerland | 13021/79 |
| Jan. 19, 1979 | [CH] | Switzerland | 566/79 |
| Jan. 19, 1979 | [CH] | Switzerland | 567/79 |
| Jun. 16, 1981 | [GB] | United Kingdom | 8118491 |

[51] Int. Cl.³ .................. A61K 9/32; A61K 9/36; A61K 9/58; A61K 9/62

[52] U.S. Cl. .................. 424/33; 424/32; 424/35

[58] Field of Search .................. 424/32, 33, 35

[56] References Cited

U.S. PATENT DOCUMENTS

| 3,035,977 | 5/1962 | Agood | 424/32 |
| 3,146,169 | 8/1964 | Stephonson et al. | 424/261 |
| 3,149,038 | 9/1964 | Jeffries | 424/32 |
| 4,078,065 | 3/1978 | Franz | 424/261 |

FOREIGN PATENT DOCUMENTS

| 2546577 | 4/1977 | Fed. Rep. of Germany. |
| 7201789 | of 0000 | France. |
| 276859 | of 0000 | Netherlands. |
| 9204 | 7/1974 | Switzerland. |
| 1456618 | of 0000 | United Kingdom. |
| 2025227 | of 0000 | United Kingdom. |
| 2048671 | of 0000 | United Kingdom. |
| 1125882 | 9/1965 | United Kingdom. |
| 1143923 | 5/1972 | United Kingdom. |

OTHER PUBLICATIONS

Technical Report, German (1978).
Derwent Abst. 488304,9/3/76 Siphar.
Pharmazeutische Zeitung, 1978, p. 1289–1295.
Chem. Abst., vol. 84 (1976), p. 126789/w Ger. Pat.
Ergot Alkaloids & Rel. Compds, B. Berds et al., 1978, pp. 742–766.
Modern Pharmaceuticals, Banker & Rhodes, pp. 44–45.
Therapie, 1979, 34, 625–634.
Pharm. Ind., 41 (9) 881–883 (1979).
Fortschr. Med. 96 (25), 1-4 (1978).
Z. Allg. Med. 54, 1454–1459 (1978).
Derwent Abstract of NL Patent 276859 (9).
Derwent Abstract 08232D of French Patent 2453642.
Boll. Chim. Farm. 1975 (114) 259.
Dictionaire Vidale 1980 p. 982.
Seglor Retard (ca. Feb. 1978).
Ther. d. Gegnw. 1970, 109, 694.

*Primary Examiner*—Stanley J. Friedman
*Attorney, Agent, or Firm*—Gerald D. Sharkin; Robert S. Honor; Walter F. Jewell

[57] ABSTRACT

The invention provides solid enteric-coated compositions in unit dose form for oral application, the core of the composition containing an ergot alkaloid and a polyalkoxyalkylene sterol ether. The compositions are characterized by a prolonged effect and a good bioavailability of the active agent. The core may be in solid solution form. The enteric-coating may also be surrounded by an outer medicament layer.

29 Claims, No Drawings

GALENICAL COMPOSITIONS

This is a continuation-in-part of our co-pending application Ser. No. 105,831 filed Dec. 20, 1979, now abandoned.

The invention provides galenical compositions for oral application of ergot alkaloids which are characterised by a prolonged effect and a good bioavailability of the active agent.

It is undisputed amongst medicinal specialists, that under many circumstances it is preferred to apply a drug once a day instead of more times a day. This may be achieved in so-called "retard systems" by retarding and delaying the release of the active agent, with the aim of producing a longer duration of therapeutic effect. In the field of the ergot therapy, a retardation with classical systems, e.g. with a matrix system or with the aid of micro-encapsulation, induces each time in important decrease of the total bioavailability.

It is also known, that ergot alkaloids are stable in the presence of acids, which means that they do not disintegrate in the gastric juices, and that the resorption of ergot alkaloids takes place mainly in the intestinal tract. Enteric coated drugs containing an ergot alkaloid are therefore not expected to provide an improved bioavailability.

It is therefore surprising that with the aid of an enteric coating thereby giving a high concentration of ergot peptid alkaloid in the intestines one observes that the duration of action of an ergot alkaloid is not only significantly prolonged but that, moreover, the total bioavailability it notably improved when the coated core contains, in addition to the ergot alkaloid, a polyalkoxyalkylene sterol ether.

The invention therefore provides, more specifically, a solid enteric-coated composition for oral application, the core of the composition containing an ergot alkaloid and a polyalkoxyalkylene sterol ether.

The invention also provides a process for the production of compositions according to the invention, by enteric coating a core comprising an ergot alkaloid and a polyalkoxyalkylene sterol ether (hereinafter designated sterol ether).

The term "core" comprises any mixture of an ergot alkaloid and a sterol ether, if desired in admixture with further physiologically acceptable material, that can be surrounded by a enteric-coating. The term "core" comprises, in a wide sense, not only tablets, pellets or granules but also capsules, e.g. soft or hard gelatine capsules containing a liquid, waxy or solid, e.g. pelleted mixture of an ergot alkaloid, a sterol ether and optionally pharmaceutically acceptable material. Such capsules may then be enteric-coated, e.g. in conventional manner. When tablet cores are used they have preferably a hardness of from ca 10 to ca 70N.

The pellets or granules may, after application of the enteric-coating, be used as such or to fill capsules, e.g. hard gelatine capsules. Suitable applications of the compositions according to the invention are therefore tablets, pellets, granules or capsules.

The pellets may be made in conventional manner, e.g. by extrusion or granulation. The pellet size may be for example from 0.5 to 1.25 mm in diameter. The pellet density is not critical, but is conveniently conventional for pellet compositions. If desired the pellets may contain besides the ergot alkaloid and sterol ether other pharmaceutical components.

The pellets may be individually enteric coated. Conveniently they are formulated in unit dosage form, e.g. in a vessel capable of dissolving in stomach or gastric juices, e.g. a hard or soft capsule, e.g. from gelatine. This form may give a particularly prolonged duration of action whilst still exhibit satisfactory bioavailability.

Alternatively the pellets may be uncoated and filled into a vessel capable of dissolving in the intestinal juices which is enteric coated. The vessel may be a hard or soft capsule, e.g. from gelatine. This form may give a particular good bioavailability as well as a prolonged duration of action.

The term solid compositions means compositions which are of a definite shape, i.e. not wholly liquid. Hence, the term solid composition covers capsules partially filled with pellets, enteric coated granules and pellets and soft gelatin capsules containing liquids.

The term "ergot alkaloids" comprises natural ergot alkaloids such as ergotamine, ergocristine, α-ergocryptine, β-ergocryptine and ergocornine, synthetic or semi-synthetic derivatives thereof such as ergovaline, co-dergocrine and dihydroergotamine in free base form or in the form of an acid addition salt with pharmaceutically acceptable organic or inorganic acids such as methanesulphonc, maleic, tartaric or hydrochloric acid.

The active agents which are of special interest for use in the invention, are compounds of formula I

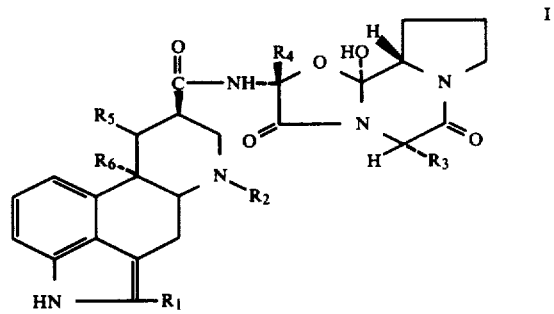

wherein
$R_1$ is hydrogen or halogen,
$R_2$ is hydrogen or $C_{1-4}$alkyl,
$R_3$ is isopropyl, sec.-butyl, isobutyl or benzyl,
$R_4$ is methyl, ethyl or isopropyl, and
either
$R_5$ is hydrogen and
$R_6$ is hydrogen or methoxy
or $R_5$ and $R_6$ together are an additional bond,
or mixtures thereof.

When $R_1$ is halogen, it is preferably bromine.

Especially preferred compositions of the invention contain co-dergocrine, bromocryptine or dihydroergotamine in free base form, or preferably, in pharmaceutically acceptable acid addition salt form as active agent.

Preferred sterol ethers for use in the compositions of the invention have a hydrophilic-liphophilic balance value (HLB group number) of from about 10 to about 20, especially from 12 to 16. Preferably they are water soluble. They preferably are ethers of lanosterol, dihydrocholesterine and, particularly, of cholesterine or phytosterine or mixtures of such ethers. Especially suitable sterol ethers are sterols etherified with an average of 8 to 75, preferably 9 to 30 alkylene oxide units. The hydroxy group in the end alkylene unit of such sterol ethers may be partially or completely acylated, e.g. by acyl radicals or aliphatic carboxylic acids, such as acetyl. Especially perferred are sterol thers etherified with ethylene oxide and/or propylene oxide units.

The sterol ethers may be obtained in conventional manner by etherifying the sterol with the corresponding amount of alkylene oxide, e.g. ethyleneoxide and optionally acylating the so obtained alcohols. They are in general available on the market and are known e.g. under the names polyethyleneglycol sterol ether or polyoxyethylene cholesterin ether, and are e.g. offered for sale by the firm Amerchol under the trade name Solulan ®. Examples of Solulan ® types which are available on the market and are suitable for use in the compositions according to the invention are such obtainable by alkoxylation of e.g.

(a) 1 mol cholesterin with about 24 mol ethylene oxide (Solulan ® C-24)
(b) 1 equivalent of lanolin alcohols with about 16 equivalents ethylene oxide (Solulan ® 16)
(c) 1 equivalent of lanolin alcohols with about 25 equivalents ethylene oxide (Solulan ® 25)
(d) 1 equivalent of lanolin alcohols with about 75 equivalents ethylene oxide (Solulan ® 75)
(e) 1 equivalent of lanolin alcohols with about 10 equivalents propylene oxide (Solulan ® PB-10) and also the
(f) partially acetylated derivative of 1 equivalent of lanolin alcohols ethoxylated with about 10 equivalents ethylene oxide (Solulan ® 98) and the
(g) completely acetylated derivative of 1 equivalent of lanolin alcohols ethoxylated with about 9 equivalents ethylene oxide (Solulan ® 97).

Further sterol ethers are offered for sale by the firm Henkel under the trade name Generol ® and by the firm Nikko Chemicals Co. Ltd. under the trade name Nikkol ®. Examples of Generol ® types are such obtainable by alkoxylation of e.g.

(h) 1 equivalent of phytosterinalcohols with about 16 equivalents of ethylene oxide (Generol ® 122 E 16)
(i) 1 equivalent of phytosterinalcohols with about 25 equivalents of ethylene oxide (Generol ® 122 E 25)

The term "about" in the above paragraphs (a) to (i) indicates that the given number of ethylene oxide or propylene oxide equivalents involved is a mean value, i.e. that some sterol ethers bear more and others less ethyleneoxy- or propyleneoxy-groups.

Lanolinalcohols are also known as wool fat alcohols [Handbuch der Kosmetika und Riechstoffe, 2. Ed. 1950, Vol. I, page 1101 (Janistyn)] and are a mixture of i.e. cholesterin, dihydrocholesterin and lanosterol.

Phytosterinalcohols may be produced from soja oil and comprise essentially sitosterol, campelsterol and stigmasterol.

The term "enteric coating" comprises any pharmaceutically acceptable coating preventing the release of the active agent in the stomach and sufficiently disintegrating in the intestinal tract (by contact with approximately neutral or alkaline intestine juices) to allow the resorption of the active agent through the walls of the intestinal tract. Various in vitro tests for determining whether or not a coating is classified as an enteric coating have been published in the pharmacopoeia of various countries.

More specifically, the term "enteric coating" according to the invention refers to a coating which remains intact for at least 1 hour, e.g. 2 hours, in contact with artificial gastric juices such as HCl of pH 1.2 at 36° to 38° C. and thereafter disintegrates with 30 minutes in artifical intestinal juices such as $KH_2PO_4$ buffered solutions of pH 6.8.

The coating is suitably selected from macromolecular polymers. Suitable polymers are listed in e.g. Hagers der pharmazeutischen Praxis, 4th Ed. Vol. 7a, pages 739 to 742 and 776 to 778, (Springer Verlag, 1971) and Remington's Pharmaceutical Sciences, 13th Ed., pages 1689 to 1691 (Mack Publ. Co., 1970) and comprise e.g. cellulose ester derivatives, cellulose ethers, acrylic resins, such as methylacrylate copolymers and copolymers of maleic acid and phthalic acid derivatives.

The preferred films are made from cellulose acetate phthalate; copolymers derived from methylacrylic acid and esters thereof, containing at least 40% methylacrylic acid; and especially hydroxypropyl methylcellulose phthalate. An example of an appropriate cellulose acetate phthalate is the marketed product CAP (Eastman Kodak, Rochester N.Y., USA). Hydroxypropyl methyl cellulose phthalates produce especially interesting compositions and examples are the marketed products HP 50 and HP 55 (Shinetsu, Tokyo, Japan).

Since a coating consisting essentially of CAP disintegrates at a higher pH as e.g. a coating consisting especially of HP 50 the release of the active agent from compositions provided with the former coating will be more delayed than from compositions provided the latter coating. In such a way, one can, by suitable selection of the coating, obtain a retard effect that takes into account the properties of the active agent involved in an optimal way.

The thickness of the coating may vary and depends inter alia on its permeability in water and acids and the desired retard effect. In general satisfactory results are obtained with a coating of 5–100 μm, preferably 20–80 μm thickness. Thus for pellets of total weight about 140 to 280 mg the film coating may be from 12 to 34 mg.

The process according to the invention may be carried out in a manner analogous to methods known for the application of an enteric-coating.

For the preparation of coated tablets, pellets or granules one proceeds e.g. by spraying the cores with a solution of the enteric coating or using fluidised bed coaters.

Suitable solvents for the enteric-coating are for example organic solvents, e.g. an alcohol such as ethanol, a ketone such as acetone, halogenated hydrocarbons such as $CH_2Cl_2$ or mixtures of such solvents, e.g. ethanol/acetone 1:1. Conveniently a softener such as di-n-butylphthalate or diethylphthalate is added to such a solution. Preferably the softener consists of 5 to 50%, e.g. 10 to 25% of the weight of the enteric film. Conveniently the cores are warmed up at 25° up to 40° C. e.g. by means of warm air of 40° up to 70° C., before spraying. To avoid sticking of the cores in the spray procedure is preferably interrupted at certain time intervals and the cores then warmed up again. The spray pressure may vary within wide ranges; in general satisfactory results are obtained with a spray pressure of from about 1 to about 3 bar. It is, however, also possible to proceed without interruption of the spray procedure, e.g. by automatic regulation of the spray amount based on the temperature of exhaust air and/or cores.

the enteric-coated compositions of the invention have the advantageous property that, after p.o. administration to man the maximum or significant concentration of the active agent in the blood plasma is obtained after about 4–8 hours, whereas the initial peak after administration of a normal composition e.g. a tablet, is already reached after 0.5–1 hour.

The prolonged duration effect of the composition of the invention is also illustrated by determination of the concentration of active agent (and metabolites) in the blood and secreted urin in that, when the plasma concentration decreases, the rate of decrease of the plasma concentration of active agent is less than the corresponding decrease rate for normal tablets.

In addition, the plasma level after administration of the compositions according to the invention is between 6 and 24 hours after application, higher than or similar to that after administration of a normal composition e.g. a tablet. This is illustrated by the area under the plasma concentration curve (AUC) and is a measure of the excellent bioavailability of the compositions of the invention.

Accordingly, the compositions of the invention show a therapeutically desirable retard effect together with an excellent bioavailability and allow consequently treatment with one or two unit dosage forms a day.

The compositions of the invention, especially the tablets may in addition be covered by an outer medicament layer. This outer layer may contain in addition to an active agent, such as an ergot alkaloid, carriers and/or fillers which are soluble or dispersible in the gastric juices such as talc, microcrystalline cellulose, magnesium stearate, mannitol, polyvinylpyrrolidone etc. Such compositions may for example be used when a rapid onset of the activity is required. The high initial concentration of the ergot alkaloid in the blood is then maintained by its sustained release out of the core in the intestinal tract.

The optimal weight ratio in the pellets of ergot alkaloid: sterol ether depends to a great extent on the physical properties of the sterol either involved, the adjuvants used and the type and the size of the composition, e.g. the amount of the abovementioned sterol ethers of the type Solulan® 16, Solulan® 25 and Solulan® C-24 is limited in view of their waxy nature.

However, in general satisfactory results are obtained when a weight ratio ergot alkaloid: sterol ether from 1:1 to 1:25, preferably from 1:2 to 1:8, especially 1:4, is used. The range 1:02 to 1:8 is especially preferred when the cores are present in solid solution form of the ergot alkaloid and especially when polyvinylpyrrolidone is used as solid solvent.

The cores may be compounded with conventional excipients, for example binding agents, lubricants, fillers and disintegrants. Suitable fillers for the preparation of tablet cores or pellets are e.g. colloidal silicium dioxide, calcium carbonate, sodium carbonate, lactose, starch, talc; suitable granulating and disintegrating agents are e.g. starch and alginic acid; suitable binding agents are e.g. starch and gelatine and suitable lubricants, stearic acid and talc. The use of cores having the ergot alkaloid in solid solution form is a special embodiment of the invention. Such cores may be prepared as follows:

An ergot alkaloid, a sterol ether and a pharmaceutically acceptable polymer which is at least partly soluble in an aqueous medium, especially a polyalkylene glycol, polyvinylpyrrolidone, a copolymer of vinylpyrrolidone and vinyl acetate or a mixture of these are mixed together.

Suitable polyalkylene glycols include polyethylene glycol and polypropylene glycol and their copolymers having a molecular weight of 200 to 20,000, preferably 4000 to 15,000, more preferably 6000 to 13,000. By "polyvinylpyrrolidone" is meant uncrosslinked poly (N-vinyl)pyrrolidone-2, suitably of molecular weight between 10,000 and 100,000, preferably 11,500 to 40,000, more preferably 20,000 to 30,000. The copolymer of vinylpyrrolidone and vinyl acetate preferably contains 60% by weight vinylpyrrolidone and 40% by weight vinyl acetate and preferably has a molecular weight of 30,000 to 100,000, more preferably 40,000 to 90,000.

When desired stabilizers such as acids, preferably methanesulphonic acid, maleic acid or tartaric acid are added to adjust the pH of the composition. The preferred pH range for the composition is pH 4–6, preferably pH 4–5.

The weight ratio ergot alkaloid: sterol ether: pharmaceutically acceptable polymer may vary between wide ranges; however, in general satisfactory results are obtained with ratios varying in the range 1:1–10:0.1–10, especially 1:2–8:0.1–10 and more preferably 1:2–5:01–5.

For the preparation of the solid solutions according to the invention the polymers are employed in solid form. In case one of the polymers used is liquid at room temperature, e.g. a polyalkylene glycol having a molecular weight of about 200, then it is obvious that such a polymer is not used alone, but in conjunction with a polymer which is solid at room temperature.

The abovementioned constituents are dissolved by stirring in a suitable solvent, for example in a lower alcohol such as ethanol or methanol, or in chloroform, at a temperature of from 30° to 70° C., preferably 40° to 60° C., and the solvent may be removed by evaporation under vacuum at the same temperature. In the preparation of the solution it is also possible to add only a part of the polymer and the additional ingredients, if any, and to add the remainder during the evaporation of the solvent. The resulting clear solution is left to solidify at room temperature (15° to 25° C.) and the solid solution or dispersion may then be ground to a fine powder and dried, suitably under vacuum at 30° C., to remove all traces of the solvent.

The solid solution obtained according to the above process is then compounded in known manner with pharmaceutically acceptable diluents or carriers, optionally with an additional amount of a sterol ether and the total content of sterol ether in the pellets should preferably lie in the above given ranges.

The following examples illustrate the invention. All temperatures are in degrees Celsius.

Polyvinylpyrrolidone is uncross-linked (N-vinyl)pyrrolidone-2, e.g. brand Kollidone, available from BASF, W. Germany.

Solulan C-24 is a polyethylene glycol ether of cholesterol = polyethoxyethylene cholesterol ether Microcristalline cellulose, is, for example, brand Avicel PH 101 from FMC corporation.

Colloidal (disperse) silicon dioxide is, for example, brand Aerosil 200, from Degussa.

Corn starch is, for example, brand Sta-Rx 1500 from Staley. Dihydroergotoxin = codergocrine

EXAMPLE 1

Tablet cores consisting of 3 g dihydroergotamine, 75 g cholesterin which is ethoxylated with about 24 ml ethylene oxide (Solulan®(C-24)) and 22 g highly dispersed silicon dioxide are heated to 30° during 10 minutes with the aid of warm air of 50° in a coating pan which is repeatedly rotated. The tablet cores are then sprayed, with the aid of a spray pistol, with a solution of 5.4 g hydroxypropyl methylcellulose phthalate (HP50) and 1.35 g di-n-butylphthalate in a 1:1 ethanol/acetone mixture, at a spray pressure of 1–1.5 bar using conventional interval spray coating procedures, and the so obtained coated tablets are then dried.

EXAMPLE 2

One proceeds analogous to Example 1, using, however, 75 g lanolin alcohols ethoxylated with about 25 equivalents ethylene oxide (Solulan® 25) instead of 75 g cholesterin ethoxylated with about 24 mol ethylene oxide.

EXAMPLE 3—Coated tablets with cores in solid solution form 15 g Co-dergocrine methane sulphonate, 1.05 g (Solulan® C-24), 33.95 g polyvinylpyrrolidone (average molecular weight 25,000) and 250 ml methanol are charged into a 1 liter round-bottomed flask. The flask is attached to a rotary evaporator and rotated at a bath temperature of 60° until the flask contents reach 60°, by which time a clear solution is obtained.

The bath temperature is maintained at 60° and the solvent evaporated under reduced pressure until the residue has a syrupy consistency. The residue is decanted into an evaporating basin and left to solidify for 2 hours at room temperature.

The solid residue is dried in a vacuum oven at 30°, ca. 1 Torr for ca. 12 hours, ground to a fine powder and dried again.

26.8 g of the so obtained solid solution are then mixed with the following adjuvants:

| | |
|---|---|
| silicon dioxide (Aerosil® 200, Degussa) | 1.0 g |
| polyvinylpyrrolidone (crosslinked) | 8.0 g |
| corn starch | 20.0 g |
| Talc | 30.0 g |
| Solulan® C-24 | 30.0 g |
| cellulose granules (Elcema G 250) | 42.0 g |
| lactose | 122.0 g | until an homogenous mixture is obtained and then pressed, in conventional manner, to tablet cores of 140.0 mg (hardness 10–32N).

The so obtained cores are then, analogous to Example 1, sprayed with a solution of

| | |
|---|---|
| cellulose acetate phthalate (CAP) | 90.0 g |
| di-n-butylphthalate | 22.5 g |
| acetone | 240.0 g |
| ethanol | 21.0 g |
| dichloromethane | 526.5 g |
| | 900.0 g | until the cores are coated with ca. 10 mg of the cellulose acetate phthalate/di-n-butylphthalate mixture per core.

The so obtained coated tablets are resistant against the gastric juices since the cores remain intact after a treatment of 1 hour with artificial gastric juices of pH=1.2. The disintegration time in artificial intestine juices is at pH 5.5 longer than 1 hour, and lies at pH 6.0 between 23–28 minutes and at pH 6.8 between 12 and 16 minutes.

EXAMPLE 4

One proceeds analogous to Example 3, spraying, however, the tablet cores of 140 mg with a solution of 140.0 g hydroxypropyl methylcellulose phthalate (HP 50) and 28 g di-n-butylphthalate in a mixture of 616 g ethanol and 616 g acetone, until the cores are coated with ca. 9 mg of the hydroxypropyl methylcellulose phthalate/di-n-butylphthalate mixture (ratio 10:2) per core.

EXAMPLE 5

Analogous to Example 3 is obtained a solid solution of 4 g of dihydroergotoxine methanesulphonate, 0.3 g Solulan® 16 and 9.1 g polyvinylpyrrolidione (average mol weight 2000).

This solid solution is then mixed with

| | |
|---|---|
| silicon dioxide | 0.5 g |
| polyvinylpyrrolidone (average mol weight 2000) | 4.0 g |
| corn starch | 10.0 g |
| talc | 15.0 g |
| Solulan® 16 | 15.0 g |
| cellulose granules (Elcema G 250) | 21.0 g |
| lactose | 61.1 g | and this mixture pressed to tablets of 140.0 mg.

The so obtained tablet cores are then sprayed, analogous to Example 4, until each core is coated either with ca 10 mg or with ca 15 mg of the mixture:hydroxypropyl methylcellulose phthalate/di-n-butylphthalate.

Analogous to the procedure described in the above Examples are obtained the tablets as listed below in Table I.

In case Ib and Ic (see table) are used, the tablet cores are in solid solution form.

TABLE I

| | EXAMPLE | 6 | 7 | 8 | 9 | 10 | 11 | 12 | 13 |
|---|---|---|---|---|---|---|---|---|---|
| Ia | Co-dergocrine mesylate | 4.0 | 4.0 | 4.0 | 4.0 | 4.0 | 4.0 | | |
| | Co-dergocrine mesylate | | | | | | | 6.0 | 6.0 |
| Ib | Solulan® C24 | 0.3 | 0.3 | 0.3 | 0.3 | 0.3 | | | 0.4 |
| Ic | Polyvinylpyrrolidone | 9.1 | 9.1 | 9.1 | 9.1 | 9.1 | | | 13.5 |
| II | Solulan® C24 | 15.0 | 15.0 | 31.7 | 7.3 | 23.7 | 15.3 | 22.9 | 22.5 |
| | Silicon dioxide | 2.4 | 2.4 | 0.5 | 0.5 | 0.5 | 0.5 | 3.6 | 3.6 |
| | corn starch | 24.0 | 24.0 | 10.0 | 10.0 | 10.0 | 10.0 | 36.0 | 36.0 |

TABLE I-continued

| EXAMPLE | 6 | 7 | 8 | 9 | 10 | 11 | 12 | 13 |
|---|---|---|---|---|---|---|---|---|
| Cellulose | 72.0 | 72.0 | 21.0 | 21.0 | 21.0 | 21.0 | 108.0 | 108.0 |
| lactose | 110.8 | 110.8 | 44.4 | 68.8 | 52.4 | 61.1 | 166.4 | 166.4 |
| Magnesium stearate | 2.4 | 2.4 | | | | | 3.6 | 3.6 |
| Kollidon CE 5050 | | | 4.0 | 4.0 | 4.0 | 4.0 | | |
| Polyvinyl-pyrrolidone (25) | | | | | | | 9.1 | 13.5 |
| talc | | | | 15.0 | 15.0 | 15.0 | | |
| HPMCP* | 26.0 | 7.0 | 7.2 | 9.0 | 9.0 | 9.0 | 7.2 | 7.2 |
| Di-n-butyl-phthalate | | | 1.8 | — | — | — | 1.8 | 1.8 |
| phthalate total weight (mg) | 266.0 | 247.0 | 149.0 | 149.0 | 149.0 | 149.0 | 369.0[1] | 369.0[1] |

*HPMCP = Hydroxypropyl methylcellulose phthalate
[1]the cores of these tablets were pressed to possess a hardness of 50–60N EXAMPLE 14: Tablet with an outer medicament layer (Mantle tablet)

(a) The cores are prepared analogous to Example 3 by mixing 26.8 g of a solid solution (consisting of 8.0 g dihydroergotamine mesylate, 0.6 g Solulan ® C-24 and 18.2 g polyvinylpyrrolidone) together with 1.0 g highly disperse silicagel, 8.0 g crosslinked polyvinylpyrrolidone, 20 g corn starch, 47.4 g Solulan ® C-24, 42.0 g cellulose granules, 104.8 g lactose and 30.0 g talc until the mixture is homogenous. The mixture is then pressed to cores of 140.0 mg.

(b) The so obtained cores are sprayed with a solution of 140.0 g hydroxypropyl methylcellulose phthalate and 28.0 g di-n-butylphthalate in a mixture of 616 g ethanol and 616 g acetone, until the cores are coated with ca. 10 mg per tablet.

(c) The outer medicament layer is prepared by mixing 4.0 g dihydroergotamine mesylate with 4.0 g disperse silica-gel, 6.0 g magnesium stearate, 166.8 g of cellulose powder, 4.0 g talc, 191.2 g corn starch and 348.0 g calcium hydrogen phosphate until the mixture is homogenous. This mixture is then pressed with the coated tablets (according to Example 14 (b) to prepare tablets with an outer medicament layer, having a total weight of 530.0 mg per tablet.

EXAMPLE 15

One proceeds analogous to any one of Examples 1 to 14, using 4 mg bromocryptine, 4 mg dihydroergovaline or 4 mg dihydroergonine instead of co-dergocrine or dihydroergotamine, and obtains tablets containing the corresponding ergot alkaloid as active agent.

EXAMPLE 16: Production of enteric coated pellets in Capsule 245 g of co-dergocrine methanesulphonate, 546 g of uncross-linked polyvinylpyrrolidone (Kollidon 25) and 16.8 g Solulan ® C-24 (a polyethylene glycol ether of cholesterol with an average ethoxylation value of 24) are mixed with alcohol and acetone(1:1 mixture) or acetone and water to produce a solution. 6.7 kg microcrystalline cellulose (Avicel PH 101) and 900 g of Solulan ® C-24 are added as well as 4 kg of alcohol. The mixture is kneaded for 10 minutes and then either granulated through a sieve (hole diameter 1.2 mm) or extruded (diameter 1 mm). The granules are left at room temperature to dry, rounded off and then warmed at 40° to 45° C. for 12 hours. The granules are sieved (hole diameter between 0.82–1.42 mm) to produce the pellets.

A dispersion of 14.4 g magnesium stearate in 300 g methanol/acaline (1:1) is produced. The mixture is homogenised and 1.2 kg hydroxypropyl methyl cellulose are added. 1 kg of the pellets are film coated using conventional fluidized bed coating procedures and dried for 12 hours.

The enteric coated pellets are then filled into hard gelatine snap fit capsules (each capsule 62 mg empty No. 2 snap fit Park-Davies).

EXAMPLE 17: Production of pellets in enteric coated capsule 129.1 g of co-dergocrine solid solution (made up from e.g. 270 g co-dergocrine methane sulphonate, 611.5 g uncross-linked polyvinylpyrrolidone and 18.9 g Solulan ® C-24), 135 g Solulan ® C-24, 2.6 g colloidal silicon dioxide are mixed, sieved and 961.7 g lactose, 585 g microcrystalline cellulose and 216 g corn starch are mixed in. To the mixture are added 21.6 g magnesium stearate. The mixture is sieved and filled into capsules No. 2 size; snap; fit Park-Davies; empty capsule weight 62 mg; full capsule weight 230 mg.

The capsules are film coated with a solution of hydroxypropyl methyl cellulose phthalate in acetone/methanol in conventional manner to produce film coating of about 32.6 mg per capsule.

The formulations of examples 18 to 25 in table II below (enteric coated pellets in capsule) are obtained analogous to the procedure described in example 16. The formulation of example 26 in the same table II (pellets in enteric coated capsule) is obtained analogous to the procedure described in example 17. The pellets are in solid solution form.

TABLE II

| Example | 18 | 19 | 20 | 21 | 22 | 23 | 24 | 25 | 26 |
|---|---|---|---|---|---|---|---|---|---|
| Co-dergocrine mesylate | 2.25 | 2.25 | 4.5 | 4.5 | 2.25 | 2.25 | 2.25 | 4.0 | 4.0 |
| Solulan ® C 24 | 0.3 | 0.3 | 0.3 | 0.3 | 0.3 | 0.3 | 0.3 | 0.28 | 0.3 |
| Polyvinylpyrrolidone | 9.1 | 9.1 | 9.1 | 10.3 | 10.3 | 9.1 | 9.1 | 9.1 | 9.1 |
| Solulan ® C 24 | 15.0 | 15.0 | 16.9 | 16.9 | 15.0 | 15.0 | 15.0 | 15.0 | 15.0 |
| Cellulose micro- | 113.35 | 113.35 | 125.5 | 125.5 | 113.35 | 113.35 | 113.35 | 111.62 | 65.0 |

TABLE II-continued

| Example | 18 | 19 | 20 | 21 | 22 | 23 | 24 | 25 | 26 |
|---|---|---|---|---|---|---|---|---|---|
| cristalline | | | | | | | | | |
| Colloidal Silicon dioxide | | | | | | | | | 2.4 |
| Lactose | | | | | | | | | 107.8 |
| Corn starch | | | | | | | | | 24.0 |
| Magnesium stearate | | | | | 0.16 | 0.16 | 0.15 | 2.0* | 2.4 |
| HPMCP** | 16.74 | 18.6 | 19.44 | 21.0 | 24.5 | 27.0 | 13.0 | 16.8 | 32.6 |
| Empty capsule | 62.0 | 62.0 | 62.0 | 62.0 | 62.0 | 62.0 | 62.0 | 62.0 | 62.0 |
| Total weight (mg) | 220.60 | 220.60 | 242.1 | 240.5 | 229.16 | 229.16 | 215.15 | 220.8 | 324.6 |

*in coating
**Hydroxypropyl methylcellulose phthalate

EXAMPLE 27

One proceeds analogous to Examples 16 to 26, using Bromocriptine, Dihydroergovaline or Dihydroergotamine instead of Co-dergocrine and obtains coated pellets containing the corresponding ergot alkaloid as active agent.

EXAMPLE 28: Clinical trial (Tablets)

The composition according to Example 4 was compared with a solid solution of dihydroergotoxine mesylate (composition A) and a conventional composition of dihydroergotoxine mesylate (composition B).

Each person treated obtained 4 mg dihydroergotoxine mesylate.

The result is listed in the following table.

| Composition | Example 4 | B | A |
|---|---|---|---|
| Concentration in Plasma after | | | |
| 20' | 0.047 ± 0.012 | 0.376 ± 0.078 | 0.215 ± 0.064 |
| 40' | 0.092 ± 0.039 | 0.472 ± 0.070 | 0.506 ± 0.049 |
| Max. conc. in plasma (ng.ml$^{-1}$) | 0.615 ± 0.077 | 0.507 ± 0.071 | 0.538 ± 0.037 |
| Time (in hours) after which max. is reached | 3.33 ± 0.48 | 0.64 ± 0.06 | 0.78 ± 0.12 |
| Bioavailability | | | |
| AUC (0–24 hours) (ng. ml$^{-1}$) | 4.778 ± 0.415 | 3.875 ± 0.279 | 3.754 ± 0.171 |
| % eliminated by urine (0–96 hours) | 1.010 ± 0.154 | 0.787 ± 0.121 | 0.740 ± 0.081 |

The good retarding effect and the excellent bioavailability of the composition according to the invention is clearly illustrated by the figures in the above table. On the other hand, we found a clearly inferior bioavailability (60–70% of composition B) when testing a marketed composition of dihydroergotoxin retarded according to conventional manner.

A marketed composition of dihydroergotamine retarded according to conventional manner, showed a bioavailability that was about 30 to 40% inferior to that found with the corresponding unretarded reference composition and inferior to compositions according to the invention.

EXAMPLE 29: Clinical trial (Pellets)

The pelleted compositions according to examples 25 and 26 were compared with a conventional tablet of co-dergocrine mesylate (composition R).

The results are given in the following table:

| Composition | % eliminated in urine (0–72 h) | time (in hours) after which max is reached | bioavailability compared with A |
|---|---|---|---|
| R | 0,759 ± 0,068 | 0–2 | 100 |
| Example 25 | 0,689 ± 0,075 | 4–6 | 92 ± 7 |
| Example 26 | 1,003 ± 0,190 | 6–8 | 134 ± 19 |

With the composition of example 25, the absorption of the active agent begins just after administration, the maximum is lower than with the reference but the rate of decrease after the maximum is less than with the reference. The bioavailability is not significantly decreased.

With the composition of example 26, the absorption of the active agent is significantly retarded and begins after ~4 hours. The absorption is then quick and intense. The bioavailability is increased.

What we claim is:

1. A solid eneric-coated composition in unit dosage form for oral application, the core of the composition containing a therapeutically effective amount of an ergot alkaloid compound of formula I,

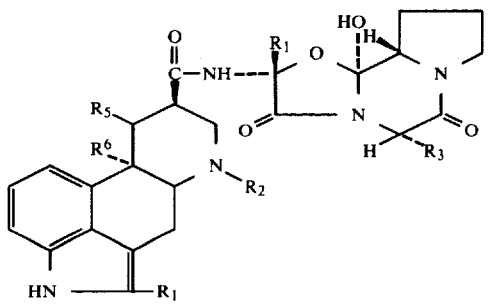

wherein
$R_1$ is hydrogen or halogen,
$R_2$ is hydrogen or $C_{1-4}$ alkyl,
$R_3$ is isopropyl, sec.-butyl, isobutyl or benzyl,
$R_4$ is methyl, ethyl or isopropyl, and
either
$R_5$ is hydrogen and
$R_6$ is hydrogen or methoxy
or $R_5$ and $R_6$ together are an additional bond
or mixtures thereof.
and a polyalkoxyalkylene sterol ether wherein the sterol part of the polyalkoxyalkylene sterol ether is chosen from the group consisting of lanosterol, dihydrochlolesterine, cholesterine and sitosterol, campesterol and stigmasterol, and wherein the enteric coating is selected from a cellulose ester derivative, a cellulose ether, an acrylic resin or a copolymer of maleic acid and phthalic acid derivatives.

2. A composition according to claim 1 wherein the sterol is chosen from lanosterol, dihydrochlolesterine and cholesterine.

3. A composition according to claim 2 wherein the ergot alkaloid is dihydroergotamine.

4. A composition according to claim 2 wherein the ergot alkaloid is dihydroergotoxine.

5. A composition according to claim 2 wherein the ergot alkaloid is bromoergocryptine.

6. A composition according to claim 2 wherein the polyalkoxyalkylene sterol ether has a hydrophilic-lipophilic balance of from 10 to 20.

7. A composition according to claim 6 wherein the polyalkoxyalkylene sterol ether has a hydrophilic-lipophilic balance of from 12 to 16.

8. A composition according to claim 2 wherein the polyalkoxyalkylene sterol ether is a sterol etherified with about 8 to about 75 alkylene oxide units.

9. A composition according to claim 8, wherein the sterol is etherified with from about 9 to about 30 alkylene units.

10. A composition according to claim 2 wherein the polyalkoxyalkylene sterol ether is a sterol etherified with ethylene oxide or propylene oxide.

11. A composition according to claim 2 wherein the enteric-coating is a cellulose acetate phthalate.

12. A composition according to claim 2 wherein the enteric-coating is hydroxypropyl methyl-cellulose phthalate.

13. A composition according to claim 2 wherein the enteric-coating is of methylacrylic acid and esters thereof, containing at least 40% methyl-acrylic acid.

14. A composition according to claim 2 wherein the enteric-coating contains a softener.

15. A composition according to claim 2 wherein the softener is di-n-butylphthalate.

16. A composition according to claim 2 in the form of a tablet.

17. A composition according to claim 2 in the form of enteric coated pellets in a capsule.

18. A composition according to claim 2 wherein the weight ratio ergot alkaloid: polyalkoxyalkylene sterol ether is from 1:2 to 1:8.

19. A composition according to claim 2 wherein the ergot alkaloid is in solid solution form.

20. A composition according to claim 19 wherein the core contains polyvinylpyrrolidone as solid solvent.

21. A composition according to claim 20 wherein the weight ratio within the core of ergot alkaloid: polyalkoxyalkylene sterol ether: solid solvent is 1:1–10: 0.1:10.

22. A composition according to claim 21 wherein the weight ratio is 1:2–8: 0.1–10.

23. A composition according to claim 22 wherein the weight ratio is 1:2–5: 0.1–5.

24. A composition according to claim 2 wherein the core contains a stabilizer.

25. A composition according to claim 24 wherein the core is stabilized at pH 4 to 6 by an acid.

26. A method for providing the sustained absorption of an ergot alkaloid comprising administering the ergot as defined in claim 1.

27. A solid enteric coated composition for oral administration in unit dosage form comprising a core containing a therapeutically effective amount of an ergot alkaloid compound selected from dihydroergotoxine, dihydroergotamine and bromocryptine and a sterol selected from lanosterol, dihydrochlolesterine or cholesterine which sterol is ethoxylated with from 9 to 35 ethylene oxide units the weight ratio of ergot alkaloid to ethoxylated sterol being from 1:2 to 1:8 and the enteric coating being selected from hydroxypropyl methyl cellulose phthalate and cellulose acetate phthalate.

28. A composition according to claim 27 wherein the ergot alkaloid is in a solid solution in polyvinylpyrrolidone.

29. A composition according to claim 27 or 28 in the form of a tablet or a capsule.

* * * * *